US011879136B2

United States Patent
Abramov et al.

(10) Patent No.: US 11,879,136 B2
(45) Date of Patent: Jan. 23, 2024

(54) METHOD FOR PRODUCING AN EXOSOME CONTAINING THERAPEUTIC AGENT

(71) Applicant: Vita Motus AG, Wattwil (CH)

(72) Inventors: Aleksandr Abramov, Moscow (RU); Alisa Petkevic, Moscow (RU); Vadim Pospelov, Kolomna (RU)

(73) Assignee: Vita Motus AG, Wattwil (CH)

( * ) Notice: Subject to any disclaimer, the term of this patent is extended or adjusted under 35 U.S.C. 154(b) by 492 days.

(21) Appl. No.: 16/668,655

(22) Filed: Oct. 30, 2019

(65) Prior Publication Data

US 2021/0040446 A1 Feb. 11, 2021

(30) Foreign Application Priority Data

Aug. 5, 2019 (CH) .......................... 988/19

(51) Int. Cl.
*C12N 5/078* (2010.01)
*A61K 35/28* (2015.01)

(52) U.S. Cl.
CPC ............ *C12N 5/0634* (2013.01); *A61K 35/28* (2013.01)

(58) Field of Classification Search
None
See application file for complete search history.

(56) References Cited

FOREIGN PATENT DOCUMENTS

RU          2593003 C2       7/2016

OTHER PUBLICATIONS

Nguyen et al. "Extracellular vesicles from bone marrow-derived mesenchymal stromal cells support ex vivo survival of human antibody secreting cells." Journal of Extracellular Vesicles 7.1 (2018): 1463778. (Year: 2018).*
Alvarez-Viejo et al. "Quantifying mesenchymal stem cells in the mononuclear cell fraction of bone marrow samples obtained for cell therapy." Transplantation Proceedings. vol. 45. No. 1. Elsevier, 2013. (Year: 2013).*
Hoffmann et al. "Comparison of in vitro-cultivation of human mesenchymal stroma/stem cells derived from bone marrow and umbilical cord." Journal of Tissue Engineering and Regenerative Medicine 11.9 (2017): 2565-2581. (Year: 2017).*
Sergeevichev et al. "Morphological and molecular analysis of angiogenesis after intramyocardial transplantation of autologous bone marrow mononuclear cells." Bulletin of Experimental Biology and Medicine 149.4 (2010): 515-520. (Year: 2010).*
Nikiforova, et al. "Rapid fluorescent visualization of multiple NAD (P) H oxidoreductases in homogenate, permeabilized cells, and tissue slices." Analytical Biochemistry 440.2 (2013): 189-196. (Year: 2013).*
Dulbecco et al., "Plaque Production by the Polyoma Virus", Virology, 1959, pp. 396-397, vol. 8.
Smith et al., "The Nucleic Acid of Polyoma Virus", Virology, 1960, pp. 185-196, vol. 12.

* cited by examiner

*Primary Examiner* — Emily A Cordas
(74) *Attorney, Agent, or Firm* — The Webb Law Firm

(57) ABSTRACT

Disclosed herein is a method for producing an exosome containing therapeutic agent, including: separating mononuclear cells from a bone marrow sample of a healthy donor; treating the separated mononuclear cells in a culture media at 37° C. and at 5% $CO_2$ for 48-72 h; separating an exosome composition from the culture media; and dissolving the separated exosome composition in a phosphate buffer to obtain the exosome containing therapeutic agent. The culture media includes a 1:1 mixture of DMEM/F12 and HEPES, 2 mmol/mL or 3.65 mg/10 mL of L-glutamine, 100 units/mL of penicillin, 100 μg/mL of streptomycin, and 10 wt % of fetal bovine serum.

6 Claims, No Drawings

METHOD FOR PRODUCING AN EXOSOME CONTAINING THERAPEUTIC AGENT

CROSS-REFERENCE TO RELATED APPLICATION

This application claims priority to Switzerland Patent Application No. 00988/19 filed Aug. 5, 2019, the disclosure of which is hereby incorporated by reference in its entirety.

FIELD OF DISCLOSURE

The present invention is directed to a method for producing an exosome containing therapeutic agent, a method for treatment with an exosome containing therapeutic agent and a culture media for producing an exosome containing therapeutic agent.

BACKGROUND, PRIOR ART

RU 2593003 C2 discloses method for treatment of tumors is known in which a patient is treated with an exosome containing medicament.

A major disadvantage of this method is its insufficient specificity, which is due to the fact that the exosomes are collected from a cell line and not from a human donor. Even leukemia cell lines do not resemble phenotypical features of a particular tumor of the patient and do not include mutations which may at least partially contribute to the development of resistance against a therapeutic agent. Furthermore, this method does not allow for restoration of the immune system, which is usually suppressed by administration of chemotherapeutic agents during treatment. K562/i-S9 cell line is used as the one that produces exosomes which are then loaded with the therapeutic agent according to RU 2593003 C2. This cell line cannot reflect the genetic and surface antigen landscape of a patient's target cells, especially if the patient has a tumor different from hemoblastosis. Exosomes which are collected from the patient's target cells cultured in vitro resemble antigen and receptor specificity of the cells these exosomes are targeted for what provides them more effective transfer to the target cells. Furthermore, these exosomes are not immunogenic as far as they are collected from autologous biomaterial.

It is an object of the present invention to provide an efficient therapeutic agent for the treatment of leukemia.

It is a further object of the invention to provide a method of treating leukaemia in a subject.

SUMMARY OF DISCLOSURE

In a first aspect, the invention is directed to a method for producing an exosome containing therapeutic agent, comprising the steps:
Separating mononuclear cells from a bone marrow sample of a healthy donor;
Treating the separated mononuclear cells in a culture media at 37° C. and at 5% CO2 for 48-72 h;
Separating an exosome composition from the culture media;
Dissolving the separated exosome composition in a phosphate buffer to obtain the exosome containing therapeutic agent.

The culture media comprises a 1:1 mixture of DMEM/F12 (Dulbecco's Modified Eagle Medium: Nutrient Mixture F-12, according to Dulbecco, R. & Freeman, G. (1959) Virology 8, 396 and Smith et al. (1960) Virology 12, 185) and HEPES (4-(2-hydroxyethyl)-1-piperazineethanesulfonic acid), 2 mmol/mL or 3.65 mg/10 mL L-glutamine, 100 units/mL penicillin, 100 µg/mL streptomycin, 10 wt % fetal bovine serum. It is understood that the method for producing an exosome containing therapeutic agent and in particular step of separating mononuclear cells from the bone marrow sample of a healthy donor, is performed in vitro.

Typically, the mononuclear cells may be collected by centrifugation.

In some embodiments, dissolving the separated exosome composition in a phosphate buffer is performed such that a ratio of 1:5 to 1:20 of separated exosome composition to phosphate buffer is obtained.

In further embodiments, separating the mononuclear cells comprises:
i. Applying the treated separated mononuclear cells in the culture media to FICOLL-Urografin (F-U) solution with a density of 1.077 g/cm$^3$, wherein the ratio of separated mononuclear cells in the culture media to the FICOLL-Urografin (F-U) is 1:3-1:4, followed by centrifugation for 20 min at 1500 rpm;
ii. Collecting an interphase ring with mononuclear cells after centrifugation;
iii. Mixing the interphase ring with a Hanks salt solution in a 1:1 ratio and centrifuging the mixture for 3 min at 1500 rpm;
iv. Optionally repeating step iii., particularly 2 or 3 times, wherein after each centrifugation mononuclear cells are separated.

Typically, the Hanks salt solution consists of 185.41 mg/l calcium chloride dihydrate, 48 mg/l disodium hydrogenphosphate, 97.72 mg/l magnesium sulfate, 400 mg/l potassium chloride, 8 g/l sodium chloride, 60 mg/l potassium dihydrogenphosphate and 1 g/l glucose.

In other embodiments, the step of separating the exosome composition from the culture media further comprises a differential centrifugation.

In some embodiments, treating the separating the mononuclear cells comprises:
i. Applying the treated separated mononuclear cells in the culture media to FICOLL-Urografin (F-U) solution with a density of 1.077 g/cm$^3$, wherein the ratio of separated mononuclear cells in the culture media to the FICOLL-Urografin (F-U) is 1:3-1:4, followed by centrifugation for 20 min at 1500 rpm;
ii. Collecting an interphase ring with mononuclear cells after centrifugation; p1 iii. Mixing the interphase ring with a Hanks salt solution in a 1:1 ratio and centrifuging the mixture for 3 min at 1500 rpm;
iv. Optionally repeating step iii., particularly 2 or 3 times, wherein after each centrifugation, an exosome composition is separated.

According to a second aspect, the invention is directed to a method of treating leukaemia in a subject, comprising:
Obtaining a bone marrow sample from a healthy donor;
Separating mononuclear cells from the bone marrow sample;
Treating the separated mononuclear cells in a culture media at 37° C. and at 5% $CO_2$ for 48-72 h;
Separating an exosome composition from the culture media;
Dissolving the separated exosome composition in a phosphate buffer to obtain the exosome containing therapeutic agent;
Administering the obtained therapeutic agent intravenously to the subject;

characterized in that the culture media comprises a 1:1 mixture of DMEM/F12 (Dulbecco's Modified Eagle Medium: Nutrient Mixture F-12, according to Dulbecco, R. & Freeman, G. (1959) Virology 8, 396 and Smith et al. (1960) Virology 12, 185) and HEPES (4-(2-hydroxyethyl)-1-piperazineethanesulfonic acid), 2 mmol/mL or 3.65 mg/10 mL L-glutamine, 100 units/mL penicillin, 100 µg/mL streptomycin, 10 wt % fetal bovine serum.

In some embodiments, dissolving the separated exosome composition in a phosphate buffer is performed such that a ratio of 1:5 to 1:20 of separated exosome composition to phosphate buffer is obtained.

In some embodiments, treating the separating the mononuclear cells comprises:
 i. Applying the treated separated mononuclear cells in the culture media to Ficoll-Urografin (F-U) solution with a density of 1.077 g/cm$^3$, wherein the ratio of separated mononuclear cells in the culture media to the Ficoll-Urografin (F-U) is 1:3-1:4, followed by centrifugation for 20 min at 1500 rpm;
 ii. Collecting an interphase ring with mononuclear cells after centrifugation;
 iii. Mixing the interphase ring with a Hanks salt solution in a 1:1 ratio and centrifuging the mixture for 3 min at 1500 rpm;
 iv. Optionally repeating step iii., particularly 2 or 3 times, wherein after each centrifugation, an exosome composition is separated.

In other embodiments, the step of separating the exosome composition from the culture media further comprises a differential centrifugation.

In some embodiments, the differential centrifugation is performed for 10 min at 3000 rpm, followed by collecting a generated first supernatant and centrifuging the first supernatant for 30 min at 10 000 rpm, followed by collecting a generated second supernatant and ultra-centrifuging the second supernatant for 2 h at 100 000 rpm, wherein after each centrifuging step, an exosome composition is separated.

According to a third aspect, the invention is directed to a culture media for producing an exosome composition, comprising a 1:1 mixture of DMEM/F12 and HEPES, 2 mmol/mL or 3.65 mg/l0 mL L-glutamine, 100 units/mL penicillin, 100 µg/mL streptomycin, 10 wt % fetal bovine serum.

The invention claimed is:

1. A method for producing an exosome containing therapeutic agent, comprising:
 separating mononuclear cells from a bone marrow sample of a healthy donor;
 treating the separated mononuclear cells in a culture media at 37° C. and at 5% $CO_2$ for 48-72 hours;
 separating an exosome composition from the culture media; and
 dissolving the separated exosome composition in a phosphate buffer to obtain the exosome containing therapeutic agent;
 wherein the culture media comprises a 1:1 mixture of Dulbecco's Modified Eagle Medium/Nutrient Mixture F-12 (DMEM/F12) and N-2-hydroxyethylpiperazine-N-2-ethane sulfonic acid (HEPES), 2 mmol/mL or 3.65 mg/10mL of L-glutamine, 100 units/mL of penicillin, 100µg/mL of streptomycin, and 10 wt % of fetal bovine serum
 wherein separating the mononuclear cells comprises:
  i) applying the mononuclear cells in the culture media to a saccharose-epichlorohydrin-copolymer, sodium amidotrizoate and meglumine amidotrizoate solution with a density of 1.077 g/cm$^3$, wherein the ratio of separated mononuclear cells in the culture media to the saccharose-epichlorohydrin-copolymer, sodium amidotrizoate and meglumine amidotrizoate solution is 1:3-1:4, followed by centrifugation for 20 min at 1500 rpm;
  ii) collecting an interphase ring with mononuclear cells after centrifugation;
  iii) mixing the interphase ring with a Hanks salt solution in a 1:1 ratio and centrifuging the mixture for 3 min at 1500 rpm; and
  iv) optionally repeating step iii), wherein after each centrifugation mononuclear cells are separated.

2. The method of claim 1, wherein dissolving the separated exosome composition in a phosphate buffer is performed such that a ratio of 1:5 to 1:20 of separated exosome composition to phosphate buffer is obtained.

3. The method of claim 1, wherein step iii) is repeated, and wherein after each centrifugation mononuclear cells are separated.

4. The method of claim 1, wherein the step of separating the exosome composition from the culture media further comprises a differential centrifugation.

5. The method of claim 4, wherein the differential centrifugation is performed for 10 min at 3000 rpm, followed by collecting a generated first supernatant and centrifuging the first supernatant for 30 min at 10,000 rpm, followed by collecting a generated second supernatant and ultra-centrifuging the second supernatant for 2 h at 100,000 rpm, wherein after each centrifuging step, an exosome composition is separated.

6. The method of claim 3, wherein step iii) is repeated two or three times.

* * * * *

UNITED STATES PATENT AND TRADEMARK OFFICE
CERTIFICATE OF CORRECTION

| | | |
|---|---|---|
| PATENT NO. | : 11,879,136 B2 | Page 1 of 1 |
| APPLICATION NO. | : 16/668655 | |
| DATED | : January 23, 2024 | |
| INVENTOR(S) | : Aleksandr Abramov et al. | |

It is certified that error appears in the above-identified patent and that said Letters Patent is hereby corrected as shown below:

In the Claims

Column 4, Line 12, Claim 1, delete "serum" and insert -- serum, --

Signed and Sealed this
Eleventh Day of June, 2024

Katherine Kelly Vidal
*Director of the United States Patent and Trademark Office*